US012642425B2

(12) United States Patent
Kawamoto et al.

(10) Patent No.: US 12,642,425 B2
(45) Date of Patent: Jun. 2, 2026

(54) ENDOSCOPE SYSTEM AND METHOD OF OPERATING ENDOSCOPE SYSTEM

(71) Applicant: FUJIFILM Corporation, Tokyo (JP)

(72) Inventors: Yuta Kawamoto, Kanagawa (JP);
Hisashi Endo, Kanagawa (JP);
Tomonori Yokota, Kanagawa (JP);
Takashi Osanai, Kanagawa (JP);
Satoshi Ozawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 498 days.

(21) Appl. No.: 18/192,789

(22) Filed: Mar. 30, 2023

(65) Prior Publication Data

US 2023/0320568 A1 Oct. 12, 2023

(30) Foreign Application Priority Data

Mar. 31, 2022 (JP) .................................. 2022-058994

(51) Int. Cl.
*A61B 1/00* (2006.01)

(52) U.S. Cl.
CPC ...... *A61B 1/00057* (2013.01); *A61B 1/00055* (2013.01); *A61B 1/00097* (2022.02)

(58) Field of Classification Search
CPC ............ A61B 1/00055; A61B 1/00057; A61B 1/00097
See application file for complete search history.

(56) References Cited

U.S. PATENT DOCUMENTS

| | | | | |
|---|---|---|---|---|
| 2003/0085994 A1* | 5/2003 | Fujita | ................. | A61B 1/00029 348/E7.088 |
| 2005/0054896 A1 | 3/2005 | Konishi | | |
| 2019/0206567 A1 | 7/2019 | Kami | | |
| 2019/0320880 A1 | 10/2019 | Takahira | | |
| 2020/0245979 A1 | 8/2020 | Shidara | | |

FOREIGN PATENT DOCUMENTS

| | | |
|---|---|---|
| JP | 2001-008167 A | 1/2001 |
| JP | 2019-187494 A | 10/2019 |

OTHER PUBLICATIONS

The extended European search report issued by the European Patent Office on Aug. 8, 2023, which corresponds to European Patent Application No. 23165422.9-1126 and is related to U.S. Appl. No. 18/192,789.

* cited by examiner

*Primary Examiner* — Aaron B Fairchild
(74) *Attorney, Agent, or Firm* — Studebaker Brackett PLLC

(57) ABSTRACT

An endoscope system includes an endoscope and a processor device. The processor device functions as an abnormality detection unit, an abnormality information generation unit, and an abnormality information management unit. The abnormality detection unit detects an abnormality of the endoscope by using information detected by an image sensor of the endoscope. The abnormality information generation unit generates abnormality information including sensor information detected by the image sensor at a time of abnormality detection and in a predetermined period before and after the abnormality detection and operating information of the endoscope. The abnormality information management unit stores the abnormality information in a memory.

11 Claims, 6 Drawing Sheets

FIG. 6

ENDOSCOPE SYSTEM AND METHOD OF OPERATING ENDOSCOPE SYSTEM

CROSS-REFERENCE TO RELATED APPLICATIONS

This application claims priority under 35 U.S.C § 119(a) to Japanese Patent Application No. 2022-58994 filed on 31 Mar. 2022. The above application is hereby expressly incorporated by reference, in its entirety, into the present application.

BACKGROUND OF THE INVENTION

1. Field of the Invention

The present invention relates to an endoscope system provided with an endoscope and a processor, and a method of operating an endoscope system.

2. Description of the Related Art

An endoscope system having an endoscope and a processor device (processor) is used for a long period by performing maintenance on a periodic basis or in a case where an abnormality has occurred. A maintenance period differs for each endoscope system, and it is difficult to properly grasp the maintenance period. Therefore, in an endoscope system described in JP2019-187494A (corresponding to US2019/320880A1), an operating status of an endoscope and an error number in a case where an error has occurred are transmitted to a server.

SUMMARY OF THE INVENTION

However, in JP2019-187494A, although it is suitable for grasping the maintenance period, there is a problem in that it is difficult to efficiently perform a repair in a case where an abnormality has occurred in an endoscope and the repair is required. That is, in a case of performing the repair, a cause and a repair location are specified while reproducing the abnormality, but only the operating status of the endoscope and the error number (type of error that has occurred) are not sufficient to reproduce the abnormality, and there is a problem in that it takes time and effort to reproduce the abnormality or in that the abnormality cannot be reproduced and a normal part may be replaced by a forecast repair.

The present invention has been made in view of the above background, and an object of the present invention is to provide an endoscope system and a method of operating an endoscope system capable of efficiently performing a repair by facilitating reproduction of an abnormality.

In order to solve the above-described problem, according to the present invention, there is provided an endoscope system comprising: an endoscope that images an inside of a body cavity; and a processor, in which the processor is configured to detect an abnormality of the endoscope by using information detected by a sensor provided in the endoscope, and store sensor information detected by the sensor at a time of abnormality detection and in a predetermined period before and after the abnormality detection and operating information including an operational status of the endoscope, in an internal memory.

The processor may be configured to transmit the sensor information and the operating information to a server connected via a network.

The processor may be configured to store an error history including a type and an occurrence timing of the detected abnormality, in the internal memory.

The processor may be configured to transmit the error history to the server.

An abnormality prediction unit that uses the information stored in the internal memory to predict an abnormality that may occur in the endoscope in future may further be provided.

A notification unit that provides a notification of a prediction result of the abnormality prediction unit may further be provided.

The notification unit may be a display device that displays the prediction result.

The operating information may include at least one of the number of uses of the endoscope or a frequency of use of the endoscope, in addition to the operational status.

The sensor may include at least one of an image sensor that performs the imaging in the endoscope, a humidity sensor that detects a humidity inside the endoscope, a torque sensor that detects an operation torque of an operation part of the endoscope, or an angle sensor that detects a direction of a distal end portion of the endoscope.

The endoscope may be provided with a plurality of sensors as the sensor, and the processor may be configured to store the sensor information for all the sensors in the internal memory in a case where the abnormality is detected.

The processor may be configured to transmit the sensor information for all the sensors to the server in a case where the abnormality is detected.

In addition, in order to solve the above-described problem, according to the present invention, there is provided a method of operating an endoscope system, comprising: a step of detecting an abnormality of an endoscope by using information detected by a sensor provided in the endoscope; and a step of storing sensor information detected by the sensor at a time of abnormality detection and in a predetermined period before and after the abnormality detection and operating information including an operational status of the endoscope, in an internal memory.

According to the present invention, the abnormality is easily reproduced, and a repair can be efficiently performed.

BRIEF DESCRIPTION OF THE DRAWINGS

FIG. 6 is a block diagram showing a function of a processor device and a configuration of an endoscope.

DESCRIPTION OF THE PREFERRED EMBODIMENTS

First Embodiment

Figure 1:
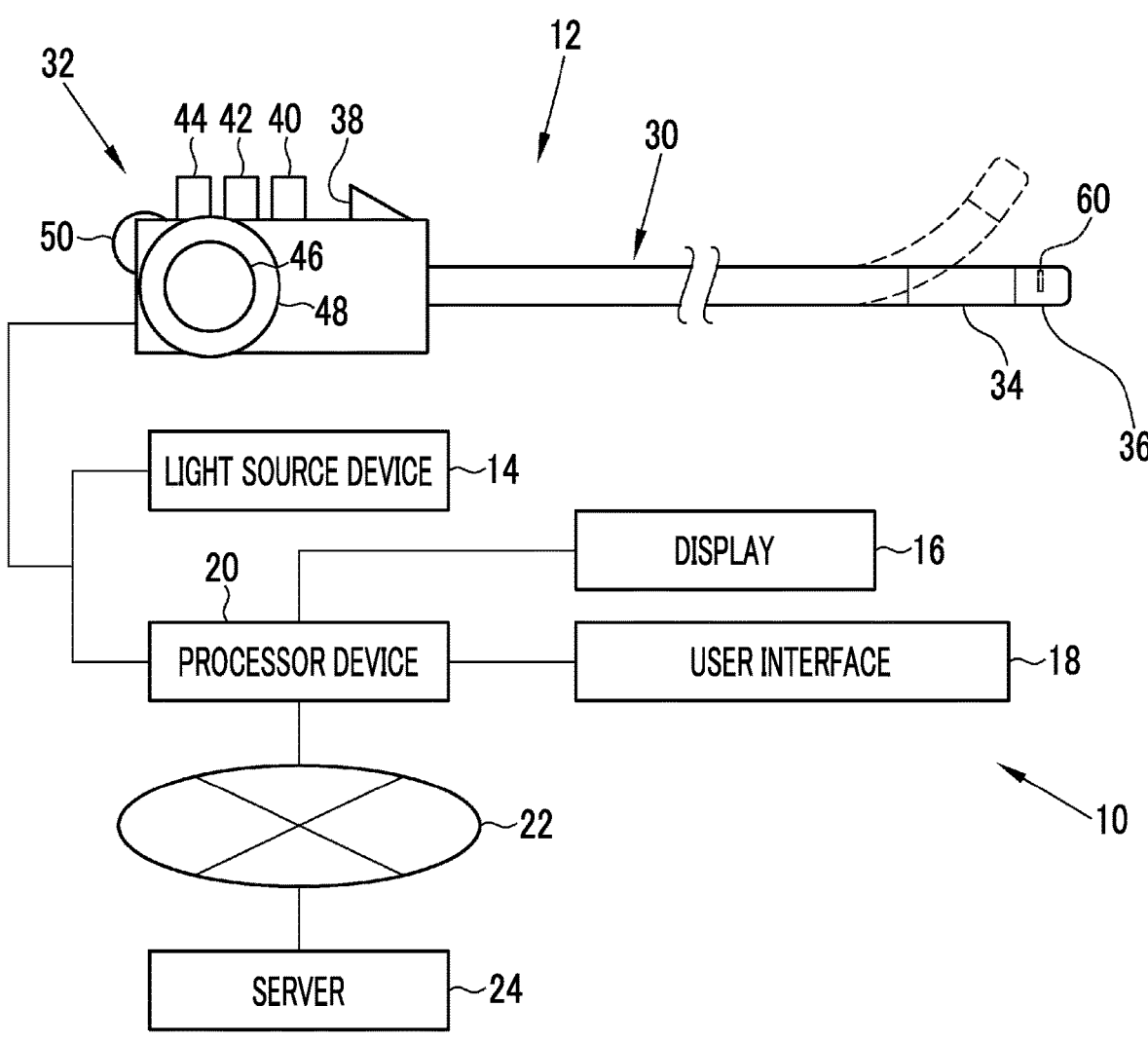
FIG. 1 is a block diagram showing a configuration of an endoscope system.

As shown in FIG. 1, an endoscope system 10 of the first embodiment includes an endoscope 12, a light source device 14, a display 16 (display device), a user interface 18, and a processor device 20 (processor).

In the endoscope system 10, the endoscope 12 is optically connected to the light source device 14 and electrically connected to the processor device 20. In addition, in the endoscope system 10, the processor device 20 is electrically connected to each unit (the endoscope 12, the light source device 14, the display 16, and the user interface 18) of the endoscope system 10. Further, in the endoscope system 10, the processor device 20 is connected to the server 24 via a network 22, such as a Local Area Network (LAN) or the Internet.

The endoscope 12 includes an insertion part 30 that is inserted into a body (body cavity) of an object to be observed, an operation part 32 connected to a proximal end side of the insertion part 30, and a bendable portion 34 and a distal end portion 36 that are provided on a distal end side of the insertion part 30. The operation part 32 is provided with an inlet 38 of a forceps channel for inserting a treatment tool, such as a forceps. In addition, the operation part 32 is provided with various operation members that receive operations from a user, such as bending of the bendable portion 34, zooming during subject imaging, a still image capturing instruction, switching of an imaging mode, and air supply and water supply. In the present embodiment, as the above-described operation members, rotary dials 40, 42, and 44 to be rotated and pressing buttons 46, 48, and 50 to be pressed are provided.

The distal end portion 36 is provided with an illumination window for emitting illumination light, an observation window for receiving reflected light that is reflected by a subject by being emitted from the illumination window, an outlet of the forceps channel, an air supply and water supply port, and the like. In addition, the distal end portion 36 includes an image sensor 60 (sensor) provided behind the observation window. The image sensor 60 is an image sensor that outputs a captured image as a digital image signal, such as a Charge Coupled Device (CCD) or a Complementary MOS (CMOS). The image captured by the image sensor 60 is input to the processor device 20.

The light source device 14 supplies illumination light to the endoscope 12. The display 16 is, for example, a well-known liquid crystal display, and displays various types of information, such as operating information, an error history, and abnormality information, which will be described later, in addition to the image captured by the endoscope 12 (image sensor 60). The user interface 18 is an input device that is used to perform input or the like to the processor device 20, and is, for example, a keyboard, a mouse, a foot pedal, a touch panel, a microphone, and/or a motion sensor.

Figure 2:
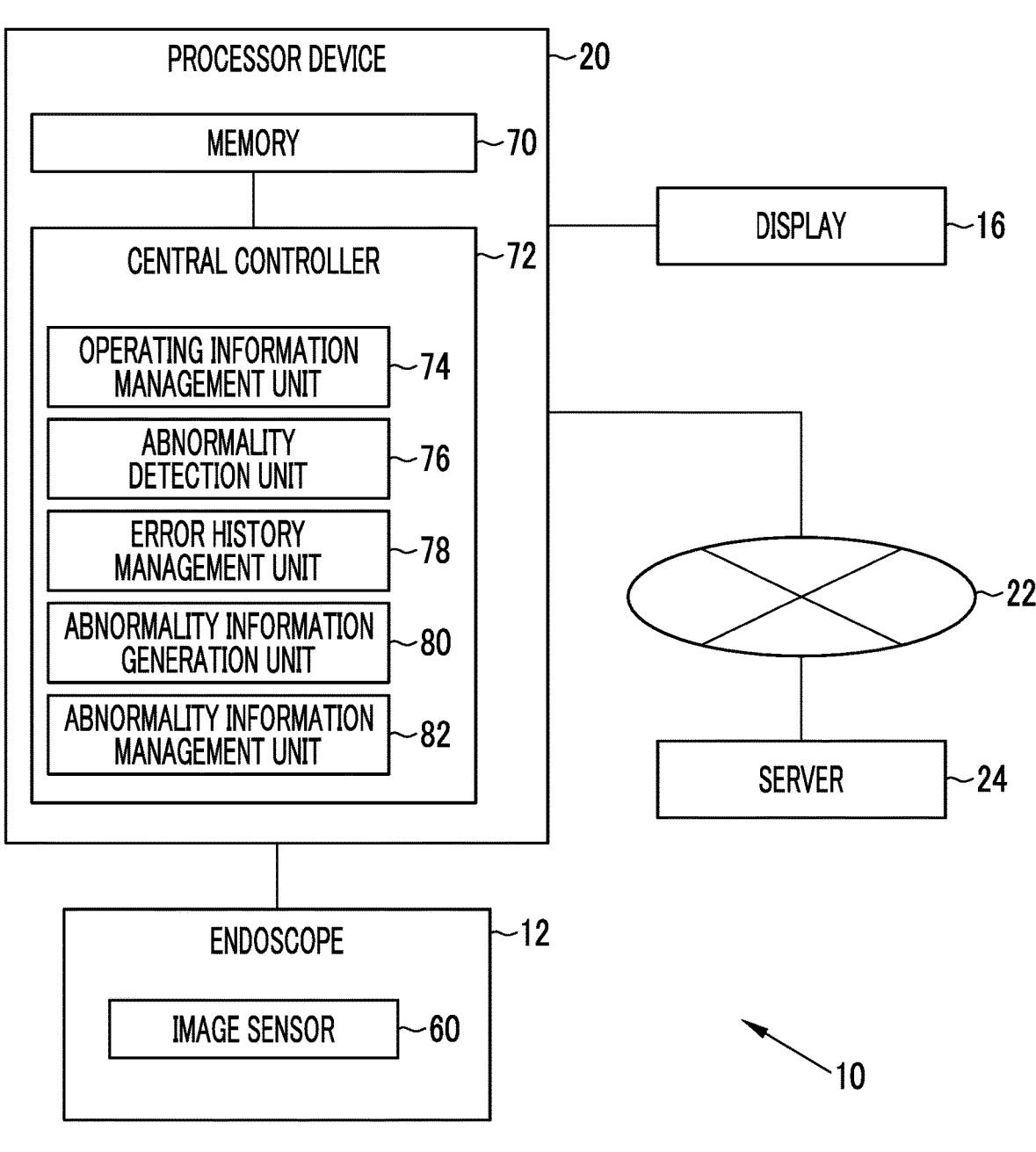
FIG. 2 is a block diagram showing a function of a processor device and a configuration of an endoscope.

As shown in FIG. 2, the processor device 20 is provided with a memory 70 (internal memory) and a central controller 72. A program related to various types of processing, control, or the like is stored in the memory 70. The central controller 72 operates the program stored in the memory 70 to function as an operating information management unit 74, an abnormality detection unit 76, an error history management unit 78, an abnormality information generation unit 80, and an abnormality information management unit 82.

The operating information management unit 74 manages the operating information of the endoscope 12. The operating information includes the number of uses, a frequency of use, an operational status, and the like of the endoscope 12. The number of uses is the number of times that endoscopy is performed using the endoscope 12. The frequency of use is the number of uses in a certain period (for example, the latest one month). The operational status indicates a content, an operation timing, and the like of an operation performed on the endoscope system 10, such as operating the operation part 32 or switching the setting in the light source device 14 or in the processor device 20. The operating information management unit 74 stores and manages the operating information in the memory 70. In addition, the operating information management unit 74 transmits the operating information to the server 24 via the network 22 and stores the operating information in the server 24. The operating information stored in the memory 70 and in the server 24 can be confirmed, for example, by being displayed on the display 16 at any timing in response to a request from the user.

The abnormality detection unit 76 detects an abnormality of the endoscope 12 by using information detected by a sensor provided in the endoscope 12. In the present embodiment, the image sensor 60 is provided as the sensor, and the abnormality detection unit 76 detects an abnormality by using the captured image captured by the image sensor 60 as the information detected by the image sensor 60. Specifically, the captured image is analyzed, for example, whether or not a captured image in which a score calculated on the basis of brightness, hue, a contour shape, or the like exceeds a predetermined threshold value (or a captured image group in which such captured images are continuous for a predetermined number of frames or more) is present is determined, and it is detected that an abnormality has occurred in the endoscope 12 in a case where determination is made that the captured image exceeding the threshold value (or the captured image group) is present.

The error history management unit 78 manages an abnormality occurrence history (error history). The error history includes a type of the abnormality detected by the abnormality detection unit 76, an occurrence timing (occurrence date and time), and device information of the endoscope 12 (which is information for specifying the endoscope 12, such as a serial number of a device, a type of the endoscope 12, and a name of a medical institution as an installation destination). The error history management unit 78 stores and manages the error history in the memory 70. In addition, the error history management unit 78 transmits the error history to the server 24 via the network 22 and stores the error history in the server 24. The error history stored in the memory 70 and in the server 24 can be confirmed, for example, by being displayed on the display 16 at any timing in response to a request from the user.

In a case where an abnormality is detected by the abnormality detection unit 76, the abnormality information generation unit 80 generates abnormality information indicating an occurrence situation of the abnormality. The abnormality information includes information managed by the error history management unit 78, that is, the type of the abnormality, the occurrence timing, and the device information of the endoscope 12. In addition, the abnormality information includes sensor information acquired by the sensor (in the present embodiment, the image sensor 60) at a time of abnormality detection and in a predetermined period before and after the abnormality detection, and operating information. Specifically, in the present embodiment, the sensor information includes a captured image (or a captured image group) determined to be abnormal and a series of captured images captured in a predetermined period (for example, 10 seconds) before and after the abnormality detection. The operating information is information which is related to the number of uses, the frequency of use, and the operational status of the endoscope 12 and which is managed by the operating information management unit 74 as described above. The abnormality information includes operating information at the time of the abnormality detection and in the predetermined period before and after the abnormality detection.

The abnormality information management unit 82 manages the abnormality information generated by the abnormality information generation unit 80. Specifically, the abnormality information management unit 82 stores and manages the abnormality information generated by the abnormality information generation unit 80 in the memory 70. In addition, the abnormality information management unit 82 transmits the abnormality information generated by the abnormality information generation unit 80 to the server 24 via the network 22 and stores the abnormality information in the server 24. The abnormality information stored in the memory 70 and in the server 24 can be confirmed, for example, by being displayed on the display 16 at any timing in response to a request from the user.

As described above, in the endoscope system 10 of the first embodiment, in a case where an abnormality is detected, the abnormality information is generated and stored in the memory 70. The abnormality information includes the sensor information detected by the sensor at the time of the abnormality detection and in a predetermined period before and after the abnormality detection, and the operating information at the time of the abnormality detection and in a predetermined period before and after the abnormality detection. Therefore, it is easy to grasp and reproduce the situation in which the abnormality has occurred, and it is possible to efficiently perform maintenance.

Second Embodiment

Figure 3:
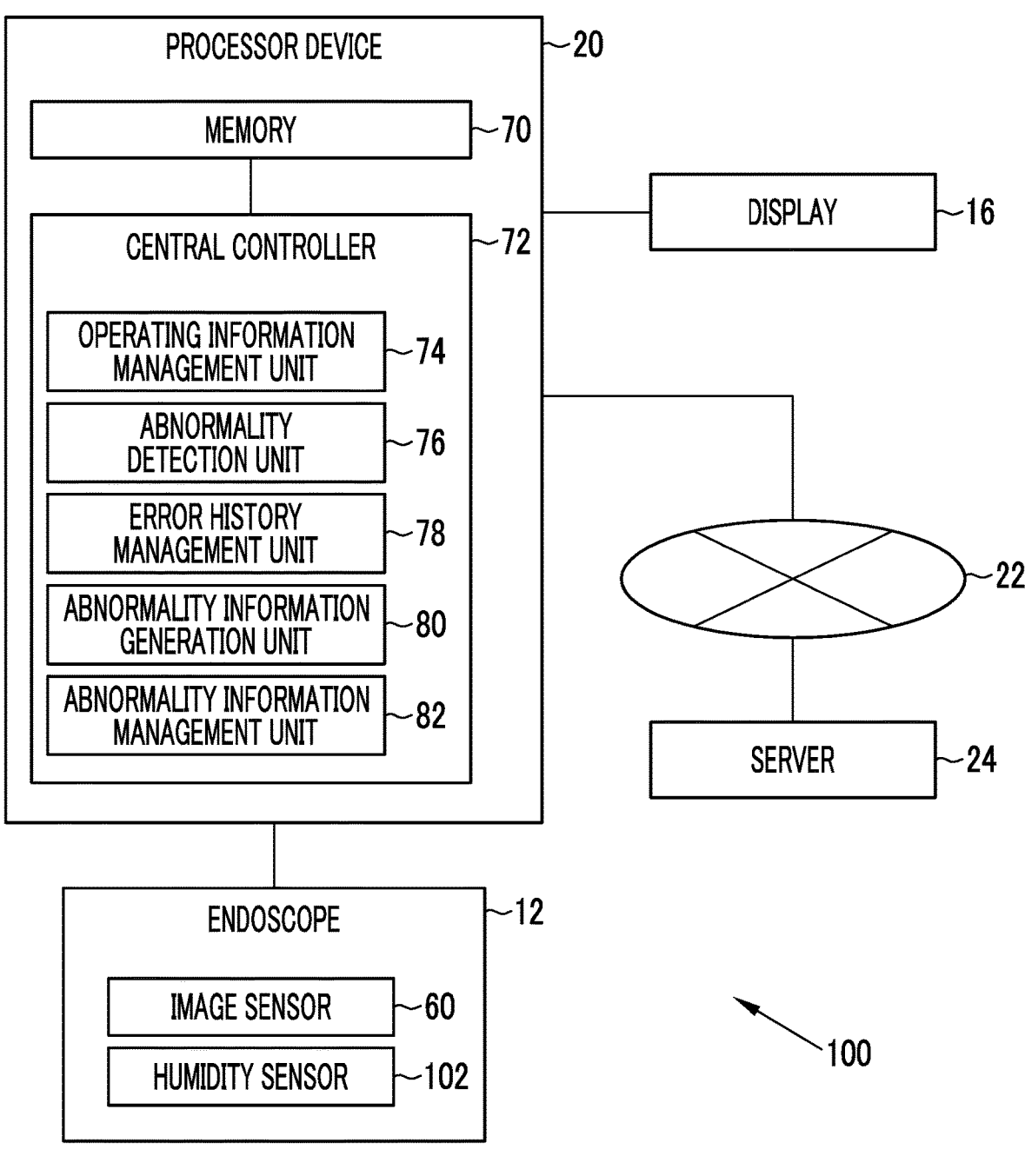
FIG. 3 is a block diagram showing a function of a processor device and a configuration of an endoscope.

As shown in FIG. 3, in the endoscope system 100 of the second embodiment, the endoscope 12 is provided with a humidity sensor 102 (sensor) in addition to the image sensor 60 described above. In the description with reference to the drawings after FIG. 3, the same reference numerals are assigned to the same members as those in the above-described embodiment, and the description thereof will not be repeated.

The humidity sensor 102 is incorporated into, for example, the insertion part 30 (distal end portion 36) and detects a humidity in the insertion part 30 (distal end portion 36). In an endoscope system 100, the abnormality detection unit 76 detects that an abnormality has occurred in the endoscope 12, for example, in a case where the humidity exceeds a predetermined threshold value on the basis of information (humidity) detected by the humidity sensor 102. In addition, the abnormality information generation unit 80 generates the abnormality information including information detected by the humidity sensor 102 at the time of abnormality detection and in a predetermined period before and after the abnormality detection, and the abnormality information generated in this manner is stored in the memory 70 and is transmitted to (stored in) the server 24 and managed by the abnormality information management unit 82.

In a case where an abnormality is detected on the basis of the information from the humidity sensor 102, the abnormality information may include information detected by a sensor other than the humidity sensor 102 (in this example, the image sensor 60) at the time of and before and after the abnormality detection. Of course, in a case where an abnormality is detected on the basis of the information from the sensor other than the humidity sensor 102, the abnormality information may include the information detected by the humidity sensor 102 at the time of and before and after the abnormality detection.

Third Embodiment

Figure 4:
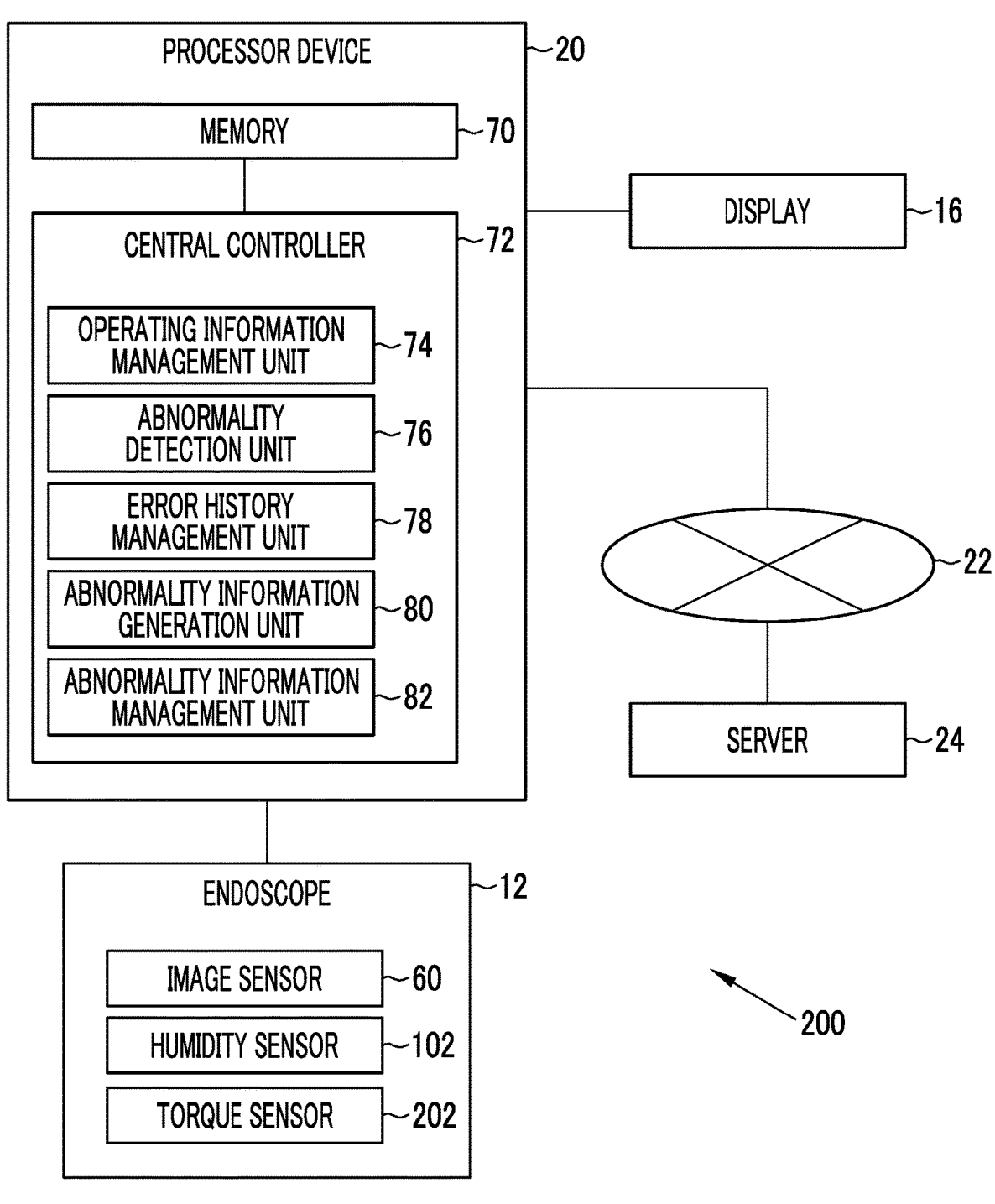
FIG. 4 is a block diagram showing a function of a processor device and a configuration of an endoscope.

As shown in FIG. 4, in an endoscope system 200 of the third embodiment, the endoscope 12 is provided with a torque sensor 202 (sensor) in addition to the image sensor 60 and the humidity sensor 102 described above. The torque sensor 202 detects an operating force applied when an operation member provided in the operation part 32 is operated, and in the present embodiment, the operating force of the rotary dial 40 for bending the bendable portion 34 is detected by the torque sensor 202.

In an endoscope system 200, the abnormality detection unit 76 detects that an abnormality has occurred in the endoscope 12, for example, in a case where the operating force exceeds a predetermined threshold value on the basis of information (operating force) detected by the torque sensor 202. In addition, the abnormality information generation unit 80 generates the abnormality information including information detected by the torque sensor 202 at the time of abnormality detection and in a predetermined period before and after the abnormality detection, and the abnormality information generated in this manner is stored in the memory 70 and is transmitted to (stored in) the server 24 and managed by the abnormality information management unit 82.

In a case where an abnormality is detected on the basis of the information from the torque sensor 202, the abnormality information may include information detected by a sensor other than the torque sensor 202 (in this example, the image sensor 60 and the humidity sensor 102) at the time of and before and after the abnormality detection. Of course, in a case where an abnormality is detected on the basis of the information from the sensor other than the torque sensor 202, the abnormality information may include the information detected by the torque sensor 202 at the time of and before and after the abnormality detection. In addition, in the present embodiment, a configuration in which the operating force of the rotary dial 40 is detected has been described as an example, but a configuration in which an operating force of another operation member is detected may be employed. Further, a configuration may be employed in which a plurality of torque sensors are provided to detect operating forces of a plurality of operation members.

Fourth Embodiment

Figure 5:
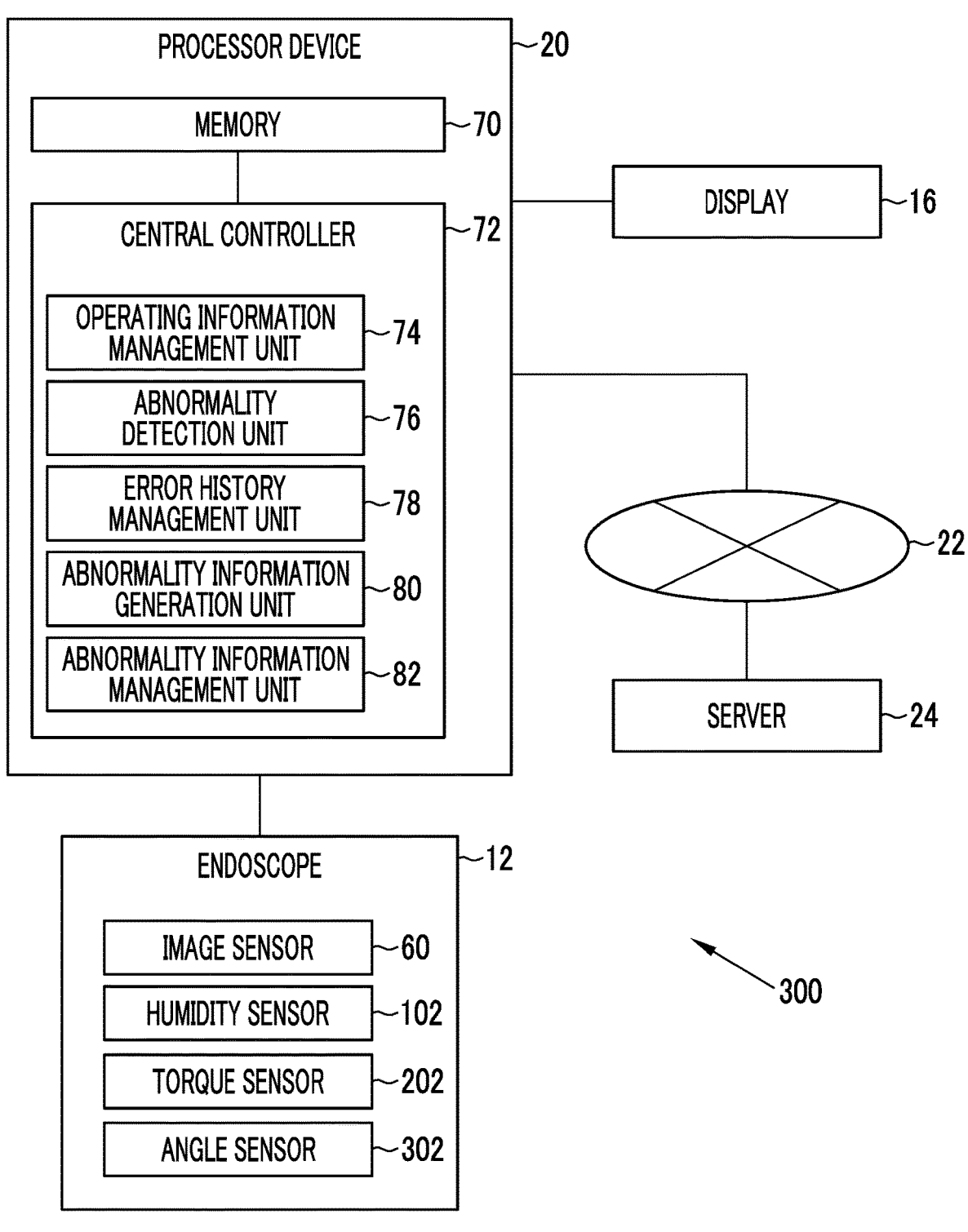
FIG. 5 is a block diagram showing a function of a processor device and a configuration of an endoscope.

As shown in FIG. 5, in an endoscope system 300 of the fourth embodiment, the endoscope 12 is provided with an angle sensor 302 (sensor) in addition to the image sensor 60, the humidity sensor 102, and the torque sensor 202 described above. The angle sensor 302 detects an angle (a bending direction and a bending amount of the bendable portion 34) of the distal end portion 36 of the endoscope 12.

In the endoscope system 300, the abnormality detection unit 76 detects that an abnormality has occurred in the endoscope 12, for example, in a case where an amount of change (direction of change) of the angle of the distal end portion 36 is different from an amount of operation (direction of operation) of the operation member for changing the angle of the distal end portion 36 by a predetermined threshold value or more on the basis of information (the angle of the distal end portion 36) detected by the angle sensor 302. In addition, the abnormality information generation unit 80 generates the abnormality information including information detected by the angle sensor 302 at the time of abnormality detection and in a predetermined period before and after the abnormality detection, and the abnormality information generated in this manner is stored in the memory 70 and is transmitted to (stored in) the server 24 and managed by the abnormality information management unit 82.

In a case where an abnormality is detected on the basis of the information from the angle sensor 302, the abnormality information may include information detected by a sensor other than the angle sensor 302 (in this example, the image sensor 60, the humidity sensor 102, and the torque sensor 202) at the time of and before and after the abnormality detection. Of course, in a case where an abnormality is detected on the basis of the information from the sensor other than the angle sensor 302, the abnormality information may include the information detected by the angle sensor 302 at the time of and before and after the abnormality detection.

In addition, in the first to fourth embodiments described above, an example in which the image sensor 60, the humidity sensor 102, the torque sensor 202, and the angle sensor 302 are provided as the sensors has been described, but a configuration may be employed in which other sensors, such as a temperature sensor, an airtightness (air pressure) sensor, and/or a current (voltage) sensor, are provided and abnormality detection and storage (management) of the abnormality information are performed by using information detected by these. Further, in the above-described embodiments, an example in which the abnormality detection and the management of the abnormality information are performed by using the information detected by the sensor provided in the endoscope 12 has been described, but a configuration may be employed in which the abnormality detection and the management of the abnormality information are performed by using information detected by a sensor provided in the light source device 14 and/or in the processor device 20.

Fifth Embodiment

Figure 6:
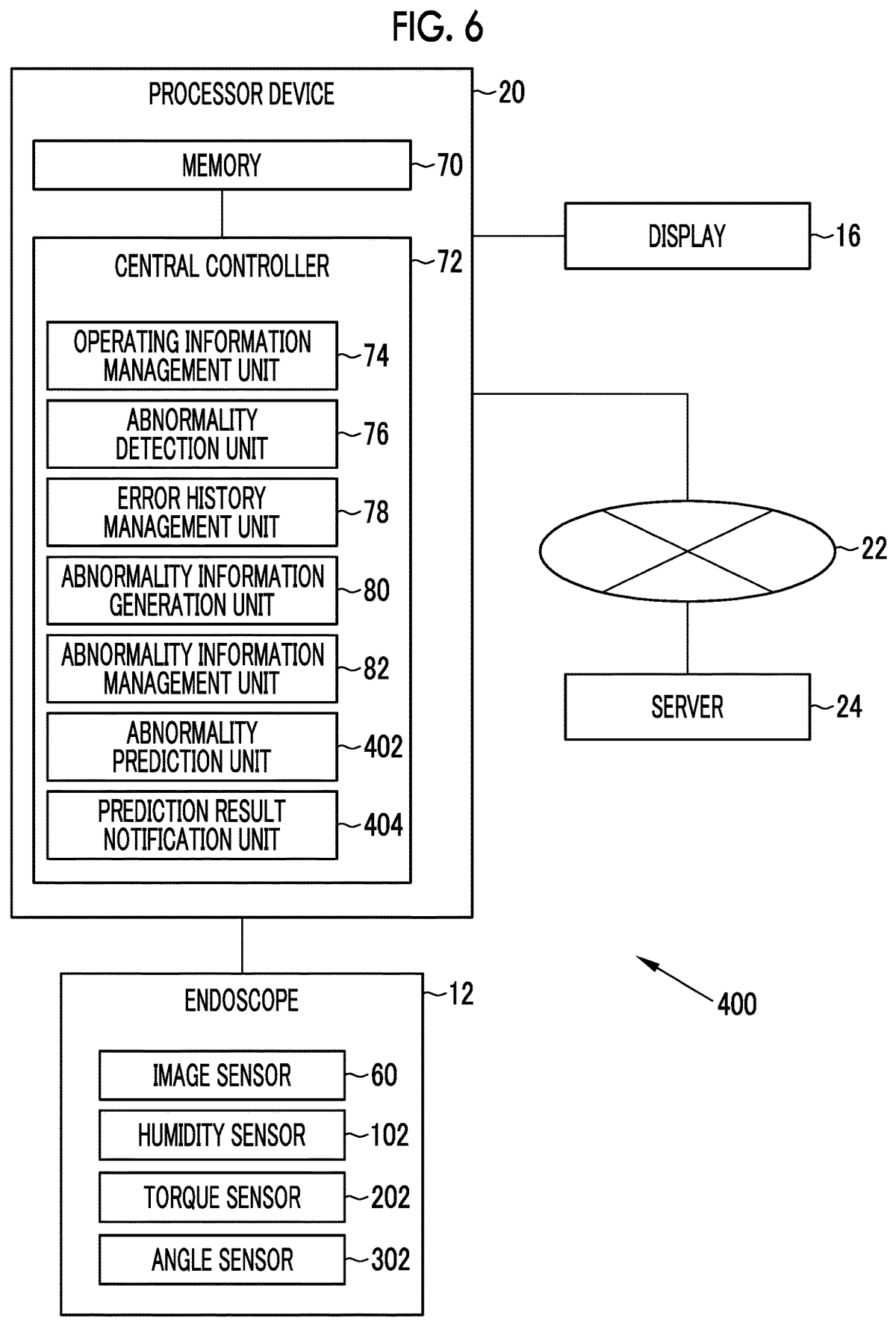

As shown in FIG. 6, in an endoscope system 400 of the fifth embodiment, the central controller 72 of the processor device 20 operates a program stored in the memory 70 to function as an abnormality prediction unit 402 (abnormality prediction unit) and a prediction result notification unit 404 (notification unit) in addition to each unit described above (the operating information management unit 74, the abnormality detection unit 76, the error history management unit 78, the abnormality information generation unit 80, and the abnormality information management unit 82).

The abnormality prediction unit 402 predicts the type and the occurrence timing of an abnormality that may occur in the endoscope 12 in the future on a periodic basis (for example, each time an endoscopy is performed or every month) and/or in response to an instruction from the user. For this prediction, the operating information, the error history, the abnormality information, and the like stored in the memory 70 are used. In addition, for this prediction, data (hereinafter, prediction data) regarding an abnormality that has occurred in another endoscope having the same type or a similar configuration is used. The prediction data is data in which a type of an abnormality that has occurred, an occurrence frequency of each abnormality, operating information at the time of occurrence of each abnormality, and the like are associated with each other. The prediction data is stored in the memory 70 in advance, and the abnormality prediction unit 402 reads out the prediction data from the memory 70 to perform the prediction. The prediction data may be stored in the server 24, and the abnormality prediction unit 402 may read out the prediction data from the server 24 to perform the prediction.

The prediction result notification unit 404 notifies the user by displaying a result of the prediction executed by the abnormality prediction unit 402 on the display 16, each time the abnormality prediction unit 402 performs the prediction, in response to an instruction from the user, and/or in a case where a period up to the occurrence timing of the abnormality predicted by the abnormality prediction unit 402 is a predetermined period (for example, half a year) or shorter. A configuration may be employed in which a speaker is provided and the notification of the prediction result is provided by a sound output from the speaker. Alternatively, a configuration may be employed in which the prediction result is transmitted to the server 24 and a server 24 side (a display, a speaker, or the like connected to the server 24) provides the notification.

In the above-described embodiments, a hardware structure of a processing unit that executes various types of processing, such as the operating information management unit 74, the abnormality detection unit 76, the error history management unit 78, the abnormality information generation unit 80, the abnormality information management unit 82, the abnormality prediction unit 402, and the prediction result notification unit 404, is various processors shown below. The various processors include, for example, a central processing unit (CPU) which is a general-purpose processor that executes software (programs) to function as various processing units, a programmable logic device (PLD) which is a processor capable of changing a circuit configuration after manufacture, such as a field programmable gate array (FPGA), and a dedicated electrical circuit which is a processor having a dedicated circuit configuration designed to execute various processing.

One processing unit may be composed of one of these various processors or a combination of two or more of the processors of the same type or different types (for example, a plurality of FPGAs or a combination of a CPU and an FPGA). Alternatively, a plurality of processing units may be composed of one processor. A first example in which a plurality of processing units are composed of one processor is an aspect in which one or more CPUs and software are combined to constitute one processor and the processor functions as a plurality of processing units, as typified by a computer, such as a client or a server. A second example is an aspect in which a processor that realizes functions of an entire system including a plurality of processing units with one integrated circuit (IC) chip is used, as typified by a system on chip (SoC) or the like. As described above, various processing units are composed of one or more of the above-described various processors, as the hardware structure.

Furthermore, as the hardware structure of the various processors, more specifically, an electrical circuit (circuitry) in which circuit elements, such as semiconductor elements, are combined is used.

In the above-described embodiments, an example in which the present invention is applied to an optical endoscope provided with the image sensor has been described, but the present invention is not limited thereto. The present invention may be applied to an ultrasonic endoscope provided with an ultrasound sensor (ultrasound probe).

In addition, in the above-described embodiment, an example in which an abnormality is detected by a common method (detection algorithm) regardless of the type of the endoscope has been described, but the present invention is not limited thereto. Different types of endoscopes (for example, an upper endoscope and a lower endoscope) may be connected and used depending on the processor device, and in such a case, it is preferable to employ a configuration in which abnormality detection algorithms are different from each other depending on the types of the endoscopes. Specifically, it is preferable to employ a configuration in which the central controller 72 (see FIGS. 2 to 6) is also made to function as a discrimination unit that discriminates the type of the endoscope connected to the processor device and the abnormality detection unit 76 detects an abnormality by using a detection algorithm corresponding to the type of the endoscope discriminated by the discrimination unit.

EXPLANATION OF REFERENCES

10, 100, 200, 300, 400: endoscope system
12: endoscope
14: light source device
16: display (display device)
18: user interface
20: processor device (processor)
22: network
24: server
30: insertion part
32: operation part
34: bendable portion
36: distal end portion
38: inlet
40, 42, 44: rotary dial
46, 48, 50: pressing button
60: image sensor (sensor)
70: memory (internal memory)
72: central controller
74: operating information management unit
76: abnormality detection unit
78: error history management unit
80: abnormality information generation unit
82: abnormality information management unit
102: humidity sensor (sensor)
202: torque sensor (sensor)
302: angle sensor (sensor)

What is claimed is:
1. An endoscope system comprising:
an endoscope configured to capture images of a body cavity; and a processor configured to:
detect an abnormality of the endoscope by using information detected by a sensor provided in the endoscope; and
store sensor information detected by the sensor at a time of abnormality detection and in a predetermined period before and after the abnormality detection and operating information including an operational status of the endoscope, in an internal memory.
2. The endoscope system according to claim 1,
wherein the processor is configured to transmit the sensor information and the operating information to a server connected via a network.
3. The endoscope system according to claim 2,
wherein the processor is configured to store an error history including a type and an occurrence timing of the detected abnormality, in the internal memory.
4. The endoscope system according to claim 3,
wherein the processor is configured to transmit the error history to the server.
5. The endoscope system according to claim 1,
wherein the processor is configured to use the information stored in the internal memory to predict an abnormality that may occur in the endoscope in future.
6. The endoscope system according to claim 5,
wherein the processor is configured to provide a notification of a prediction result of the abnormality.
7. The endoscope system according to claim 6, further comprising:
a display device that displays the prediction result.
8. The endoscope system according to claim 1,
wherein the operating information includes at least one of the number of uses of the endoscope or a frequency of use of the endoscope, in addition to the operational status.
9. The endoscope system according to claim 1,
wherein the sensor includes at least one of an image sensor configured to perform the imaging in the endoscope, a humidity sensor configured to detect a humidity inside the endoscope, a torque sensor configured to detect an operation torque of an operation part of the endoscope, or an angle sensor configured to detect a direction of a distal end portion of the endoscope.
10. The endoscope system according to claim 1,
wherein the endoscope is provided with a plurality of sensors as the sensor, and
the processor is configured to store the sensor information for all the sensors in the internal memory in a case where the abnormality is detected.
11. The endoscope system according to claim 10,
wherein the processor is configured to transmit the sensor information for all the sensors to the server in a case where the abnormality is detected.

* * * * *